(12) United States Patent
Negre (10) Patent No.: US 11,197,983 B2
(45) Date of Patent: Dec. 14, 2021

(54) DEVICE FOR ADJUSTING A DRAINAGE VALVE

(71) Applicant: SOPHYSA, Orsay (FR)

(72) Inventor: Philippe Negre, Paris (FR)

(73) Assignee: SOPHYSA, Orsay (FR)

( * ) Notice: Subject to any disclaimer, the term of this patent is extended or adjusted under 35 U.S.C. 154(b) by 351 days.

(21) Appl. No.: 16/481,223

(22) PCT Filed: Feb. 1, 2018

(86) PCT No.: PCT/EP2018/052544
§ 371 (c)(1),
(2) Date: Jul. 26, 2019

(87) PCT Pub. No.: WO2018/141859
PCT Pub. Date: Aug. 9, 2018

(65) Prior Publication Data
US 2019/0388660 A1 Dec. 26, 2019

(30) Foreign Application Priority Data
Feb. 1, 2017 (FR) ...................................... 1750840

(51) Int. Cl.
*A61M 27/00* (2006.01)
*A61M 39/22* (2006.01)
(52) U.S. Cl.
CPC .......... *A61M 27/006* (2013.01); *A61M 39/22* (2013.01); *A61M 2205/3515* (2013.01)
(58) Field of Classification Search
CPC ............... A61M 27/006; A61M 39/22; A61M 2205/3515
See application file for complete search history.

(56) References Cited

U.S. PATENT DOCUMENTS

2007/0093741 A1\* 4/2007 Miethke ............. A61M 27/006
604/9
2010/0249690 A1\* 9/2010 Soares ............... A61M 27/006
604/9

(Continued)

FOREIGN PATENT DOCUMENTS

EP 688575 A1 12/1995
EP 2236169 A1 10/2010

(Continued)

OTHER PUBLICATIONS

International Search Report corresponding International application PCT/EP2018/052544 dated May 23, 2018, 5 pages.

*Primary Examiner* — Benjamin J Klein
(74) *Attorney, Agent, or Firm* — Cooper Legal Group, LLC; Ronald M. Kachmarik (57) ABSTRACT

A device and associated method for adjusting the opening pressure of an implantable valve. The valve has a rotor of rotation axis, whose angular position determines the opening pressure. The rotor has a rotor micro-magnet movable between positions of locking and unlocking, in which positions the micro-magnet respectively prohibits and permits the rotation of the rotor. The method includes: arranging a locator to align an axis of a locator receptacle with the rotation axis and to orient the locator in an angular position; determining the angular position of the rotor about its rotation axis with respect to the locator; inserting an actuator into the locator receptacle as far as a first insertion depth; partially withdrawing the actuator from the locator receptacle as far as a second insertion depth less than the first insertion depth; rotating the actuator starting from the second insertion depth; separating the actuator from the valve.

12 Claims, 5 Drawing Sheets

(56) References Cited

U.S. PATENT DOCUMENTS

| | | | | |
|---|---|---|---|---|
| 2011/0105994 A1* | 5/2011 | Ginggen | ................ | F16K 31/08 |
| | | | | 604/9 |
| 2012/0046595 A1* | 2/2012 | Wilson | ................ | F16K 31/088 |
| | | | | 604/9 |
| 2014/0276339 A1* | 9/2014 | Wilson | ................ | F16K 37/0041 |
| | | | | 604/9 |
| 2015/0094643 A1* | 4/2015 | Soares | ................ | A61M 27/006 |
| | | | | 604/9 |
| 2016/0220794 A1* | 8/2016 | Negre | ................ | A61M 27/006 |

FOREIGN PATENT DOCUMENTS

| | | |
|---|---|---|
| EP | 2316522 A1 | 5/2011 |
| EP | 2192944 B1 | 12/2011 |
| EP | 2420284 A2 | 2/2012 |
| EP | 2777751 A2 | 9/2014 |
| EP | 2865408 A1 | 4/2015 |
| EP | 3046614 B1 | 5/2018 |

\* cited by examiner

DEVICE FOR ADJUSTING A DRAINAGE VALVE

TECHNICAL FIELD

The present invention relates to a method for adjusting a drainage valve intended for therapeutic applications, in particular the treatment of hydrocephalus, and to a device for performing such adjustment.

PRIOR ART

The treatment of hydrocephalus involves diverting cerebrospinal fluid (CSF), contained in the cerebral ventricles or the lumbar subarachnoid space, to a resorption site, for example the peritoneal cavity.

The European patent EP 688 575 from the present applicant discloses a valve suitable for this treatment. In particular, the valve has
- a body defining a substantially cylindrical and flat internal chamber,
- an admission conduit and a discharge conduit that are formed in the side wall of said chamber and are able to be connected, respectively, to a liquid delivery catheter and a liquid drainage catheter,
- a rotor able to turn in said chamber about its central axis,
- a shutter, called a "non-return valve", such as a ball, arranged at the inner end of the admission conduit,
- an elastic return member, in this case a spring with a curved leaf, of preferably semi-circular shape, fixed to said rotor, parallel to the side wall of the chamber and compressing the shutter in its seat in such a way as to regulate and, if appropriate, block the passage of liquid into the chamber via the admission conduit.

The rotation of the rotor causes the sliding of the contact point of the ball on the leaf spring and therefore causes a modification of the opening pressure.

The valve of EP 688 575 has two micro-magnets mounted in the rotor and disposed on either side of the central axis of the chamber. These two micro-magnets can be magnetically coupled to a magnetic key, called an "external device for adjusting the valve" in EP 688 575, manipulated by an operator. The magnetic key has a magnetic bar composed of a combination of magnets. The magnetic key thus makes it possible from the outside, through the cutaneous tissue, to modify the angular position of the rotor, and hence the minimum pressure allowing the liquid to move the shutter in order to free the admission conduit, called the "opening pressure".

The micro-magnets of the rotor are linearly movable in said rotor in a substantially radial direction thereof. In the absence of the key, the two micro-magnets are held, for example by mutual attraction, in a position of locking of the rotor. In particular, the two micro-magnets can maintain respective lugs in cavities formed circularly in the chamber. Under the magnetic effect of the key, the two micro-magnets move to a position of unlocking of the rotor, for example by withdrawing said lugs from said cavities.

The same key can advantageously be used to unlock the rotor and then to drive it in rotation.

In practice, the inventor has found that the driving of the rotor is not always reliable. Moreover, the unlocking can be laborious, even with a magnetic key of high power. There is therefore a need for an adjustment method and an adjustment device that are more reliable.

An object of the present invention is to respond at least partially to this need.

SUMMARY OF THE INVENTION

The invention provides a method for adjusting the opening pressure of an implantable valve, intended in particular for the treatment of hydrocephalus, in particular a valve described in EP 688 575 or in EP 3 046 614, said valve having a rotor of rotation axis R, whose angular position determines said opening pressure, said rotor having a rotor micro-magnet movable between positions of locking and unlocking of said rotor, in which positions said micro-magnet respectively prohibits and permits the rotation of said rotor, the method comprising the following successive steps:
a) arranging a locator in such a way as to align an axis X of a locator receptacle, formed in the locator, with the rotation axis R of the rotor and to orient the locator in a predefined angular position about the rotation axis R;
b) determining the angular position of the rotor about its rotation axis R with respect to the locator;
c) inserting an actuator, having a magnet, into the locator receptacle, along the axis X, as far as a first insertion depth;
d) partially withdrawing said actuator from the locator receptacle, along the axis X, as far as a second insertion depth less than the first insertion depth;
e) rotating said actuator starting from the second insertion depth, preferably maintaining said actuator at said second insertion depth;
f) separating the actuator from the valve, preferably by complete withdrawal of the actuator from the locator receptacle.

Surprisingly, the inventor has found that, depending on the insertion depth, the magnetic coupling effect between the micro-magnet of the rotor and the magnet of the actuator is more favorable for unlocking or driving the rotor. In particular, the first insertion depth is particularly favorable for unlocking, while the second insertion depth is more favorable for driving the rotor. In practice, it therefore suffices for the operator to press on the actuator in order to unlock it, then withdraw it partially before turning it to adjust the opening pressure.

Preferably, at step a), in order to reach said predefined angular position, said valve is arranged in a window of the locator, said window being configured in such a way that, when said valve is housed therein, orientation axes $O_V$ and $O_L$ of the valve and of said window are substantially parallel to one another, and the rotation axis R of the rotor of the valve and the axis X are substantially coincident.

In one embodiment, the method according to the invention is used for adjusting a valve implanted under the skin of a patient.

The invention also relates to a device for adjusting the opening pressure of an implantable valve, in particular for the treatment of hydrocephalus. The device has:
- a valve locator defining a locator receptacle of axis X;
- a key having an actuator with an actuator magnet, the actuator being insertable, along the axis X, into the locator receptacle to a first insertion depth and to a second insertion depth less than the first insertion depth;

the device having a guide for guiding the rotation of the actuator about the axis X from at least one angular position of the actuator about the axis X, preferably from any angular position of the actuator about the axis X, in which the actuator is at the second insertion depth, preferably in a rotation plane substantially perpendicular to the axis X.

Thus, from at least one angular position of the actuator, the operator can turn said actuator about the axis X in a guided manner. The movement of the actuator during this rotation is not necessarily a simple rotation about the axis X but instead can be combined, for example, with a translation along the axis X and/or another rotation. Preferably, however, the movement of the actuator during this rotation is a simple rotation about the axis X.

The term "guiding" means that the operator seeking simply to turn the actuator about the axis X gives the actuator a predetermined movement. The operator may, however, abandon the guiding. For example, in the embodiment described in detail below, he can press on the actuator in order to drive it into the locator receptacle.

A device according to the invention can in particular be used to implement an adjustment method according to the invention.

It can also have one or more of the following optional features:
- the device has a guide for guiding the rotation of the key about the axis X from at least one angular position of the actuator about the axis X, preferably from any angular position of the actuator about the axis X, to the first insertion depth, preferably in a plane of rotation perpendicular to the axis X;
- the difference between the first and second insertion depths, measured along the axis X, is greater than 2 mm, 3 mm, 4 mm, 5 mm and/or less than 15 mm, 12 mm, 10 mm, 8 mm, 7 mm or 6 mm;
- the key has a booster on which the actuator is mounted movably in translation along an axis Y of the key, which axis Y coincides with the axis X of the locator receptacle when the key is inserted into the locator receptacle;
- the actuator is guided in translation on the booster, along the axis Y;
- the device has a first stop, or "downward stop" or "lower stop", limiting the insertion of the actuator into the locator receptacle, preferably irrespective of the angular position of the actuator about the axis X, said first stop defining the first insertion depth and preferably being formed by a bottom of the locator receptacle or by a bottom of the booster of the key;
- the device has a second stop, or "upward stop" or "upper stop", defining the second insertion depth and limiting the withdrawal of the actuator from the locator receptacle and/or guiding the rotation of the actuator at the second insertion depth;
- said second stop constitutes said guide for guiding the rotation of the actuator about the axis X;
- the device preferably has a spring, more preferably a retractable spring, compressible under the effect of a push for inserting the actuator into the locator receptacle, and maintaining the actuator at the second insertion depth in the absence of said push;
- said spring preferably extends along an axis substantially parallel to the axis X and/or the axis Y;
- the first stop and/or the second stop are preferably formed so as to be active independently of the angular position of the actuator about the axis X;
- the key preferably has a booster on which the actuator is movable along the axis Y, and said spring is interposed between the actuator and the booster or between the actuator and the locator, in such a way as to oppose an insertion of the actuator, along the axis Y, beyond the second insertion depth;
- the actuator has a set of magnets that are arranged in a Halbach configuration;
- the actuator has a support on which said actuator magnet is rigidly fixed, a flange mounted movably in translation, along the axis Y, with respect to the booster, and means for preventing any displacement of the support, along the axis Y, with respect to the flange, while permitting a displacement of the support perpendicularly to the axis Y with respect to the flange.

The features described above can be combined with each other or with one or more of the features below.

The invention relates also to a treatment device having an implantable valve having:
- a body defining an internal chamber,
- an admission conduit and a discharge conduit that are formed in the side wall of said internal chamber and are able to be connected, respectively, to a liquid delivery catheter and a liquid drainage catheter,
- a rotor able to turn in said internal chamber about a rotation axis R, the rotor having a micro-magnet movable between positions of locking and unlocking of the rotor, in which positions it respectively prohibits and permits the rotation of said rotor,
- a shutter,
- an elastic return member compressing the shutter in its seat in such a way as to regulate and, if appropriate, block the passage of liquid in the internal chamber, and
- a device for adjusting the opening pressure of said valve, the adjustment device being according to the invention.

The valve can in particular have one or more of the features of the valves described in EP 688 575 or in EP 3 046 614. In particular, it preferably has exactly two micro-magnets mounted in the rotor and disposed on either side of the axis of the rotor.

A rotation of the rotor, preferably any rotation of the rotor, modifies the compression of the shutter by the elastic return member and thus modifies the opening pressure of the valve.

Preferably, the rotor is only movable in rotation about the rotation axis. In particular, it is not movable in translation along this axis.

In a preferred embodiment, the actuator magnet exerts a magnetic field designed, when the locator is placed against the skin of a patient under which the valve has been implanted, the valve being placed in the window of the locator, to unlock the rotor at the first insertion depth and to be rotationally coupled to the rotor at the second insertion depth.

Preferably, the actuator magnet is configured to exert a magnetic field designed, when the valve is in the open air and the locator is placed perpendicularly to the rotation axis of the rotor of the valve,
- to unlock the rotor only when the actuator magnet is at a distance from the rotor of less than 20 mm, 15 mm, 12 mm or even 10 mm; and/or
- to be rotationally coupled to the rotor only when the actuator magnet is at a distance from the rotor of less than 30 mm, 25 mm, 20 mm, 18 mm or 16 mm.

DEFINITIONS

The adjectives "upper", "lower", "bottom" or "top" or the prepositions "above" and "below" refer to positions relative to the vertical direction, represented by the direction V in FIG. 1b, parallel to the axis X.

Unless indicated otherwise, the verbs "have", "include" or "comprise" must be interpreted broadly and in a non-limiting sense.

Unless indicated otherwise, "cylindrical" refers to a cylinder of circular cross section.

A displacement is called "indexed" or "discrete" when it is effected step by step, that is to say by "jumps" between two successive indexing positions.

A component is called "retractable" when it is able to retreat into another component so as to no longer protrude from the surface of this other component.

A "downward" stop is a member limiting the insertion of the actuator into the locator receptacle.

An "upward" stop is a member limiting the withdrawal of the actuator from the locator receptacle, and in particular its withdrawal from the booster.

Unless indicated otherwise, a hole can be a through-hole or a blind hole.

A first component is configured to guide a second component when it can impose a displacement of this second component. The technical solutions to ensure guiding in translation and/or in rotation of one component with respect to another are well known to a person skilled in the art. The invention is not limited to one particular technical solution.

"A rotation starting from an insertion depth" of the actuator is a rotation starting in a position of the actuator in which it is inserted to said insertion depth, independently of the angular position of the actuator.

An orientation axis of the locator is a locator axis which can be used to define the angular position of the locator with respect to the valve. Similarly, an orientation axis of the valve is a valve axis which can be used to define the angular position of the valve with respect to the locator.

The "opening pressure" corresponds, in a position of the rotor of the valve, to the minimum pressure needed to move the shutter counter to the stress that the elastic return member exerts on the shutter.

A "spring" is understood as any elastic means, in particular a helical spring, a leaf spring or a block of elastically deformable material.

The term "micro-magnet" is used for clarity, in order to distinguish the magnets of the rotor from those of the actuator. The magnets of the rotor are in fact much smaller than those of the actuator, as is shown in the figures. Hence, "micro" is not limiting.

BRIEF DESCRIPTION OF THE FIGURES

Other features and advantages of the invention will become clear from reading the following detailed description and by examining the detailed drawing, in which.

Each figure includes
a perspective view (labeled "a"),
a sectional view along the section plane shown in the "c" view (labeled "b"), and
a plan view (labeled "c").

In the various figures, identical references have been used to designate identical or similar elements.

DETAILED DESCRIPTION

Valve

The valve 2 shown is a valve of the type that is described in EP 688 575 or in EP 3 046 614.

In the figures, for the sake of clarity, only the body 4, the rotor 5 and the two micro-magnets 6 of the rotor 5 have been shown. EP 688 575 and EP 3 046 614 describe in detail the operation of such valves.

Device

The adjustment device according to the invention shown has a locator 12, optionally a reading instrument, typically a compass (not shown), and a key 16 or "adjustment instrument".

Locator

The locator 12, sometimes called a "selector" or "locating instrument", has the general shape of a dish with axis X. It has a bottom 22 extending perpendicularly to the axis X and defining an upper surface $22_s$ and a lower surface $22_i$ which are substantially flat. A window 26 is cut out substantially at the center of the bottom 22.

The window 26 has the general shape of the valve 2 seen from above and, preferably, of the accessories optionally connected to the valve, in particular an upstream reservoir and a downstream anti-siphon device. The dimensions of the window are adapted so as to be able to locate by palpation, through the window, the valve and said accessories, which allows the locator to be positioned in a precise position with respect to the valve, even without noticing said valve. In particular, the axes defining the length of the window 26 and of the valve 2 (axis joining the inlet and the outlet of the valve 2) constitute orientation axes $O_L$ and $O_V$, respectively, which can thus be easily oriented parallel to each other as in FIGS. 1 to 6. The window 26 is thus a locating hole.

In one embodiment, reliefs 28 protrude from the lower surface 22i, so as to improve the positioning of the locator 12 on the valve. The reliefs preferably delineate the impression of the valve, which improves the immobilization of the locator with respect to the valve. However, the lower surface 22i is preferably flat, which minimizes the distance between the bottom of the locator and the valve and thus facilitates the adjustment of the valve.

The bottom 22 is surrounded by a cylindrical side wall 32 of axis X, which extends upward from the bottom 22, at the periphery of the bottom 22. As is explained in detail below, the side wall 32 defines a locator receptacle 34 configured to guide the insertion of the key 16 along the axis X and the rotation of said key about the axis X.

The side wall 32 defines a radially inner surface $32_{ri}$ and a radially outer surface $32_{re}$. Guide grooves 38, extending parallel to the axis X and regularly distributed about the axis X, are formed on the radially inner surface $32_{ri}$, for example at every 15 degrees. These grooves are configured to cooperate with two elastically retractable balls aligned along a diameter and projecting from the side surface of the key. During the rotation of the key, the balls retract between two consecutive positions in which said balls penetrate into guide grooves 38. The angular offset between two consecutive angular positions is 15°, for example. During the rotation of the key, the operator is alerted, by an audible click and/or by a tactile feel caused by the engagement of the balls in the guide grooves, each time one of said angular positions is reached.

The upper face of the side wall 32 has a reading zone 40 bearing position marks 42, which are uniformly distributed about the axis X, preferably 360 degrees about the axis X. The angular offset between two position marks 42 preferably corresponds to the angular offset between two guide grooves 38. The position marks 42 preferably represent opening pressure values. In this case, these position marks show that the opening pressure of the valve can be adjusted to a value of between 20 and 420 mmH$_2$O.

An alignment marker 43 or "orientation arrow", in this case superimposed on the mark "140 mmH$_2$O", indicates the direction of the window 26, which allows the locator to be oriented in the direction of flow of the liquid.

In the embodiment shown, a rotary ring 44 is mounted movably in rotation about the axis X on the side wall 32. The rotary ring 44 carries a position marker 45 that the operator can place opposite one of the position marks 42. In FIG. 1a, the position marker 45 has thus been placed opposite position mark "70". Preferably, the displacement of the rotary ring 44 is indexed, preferably in such a way that the position marker 45 can only be positioned opposite position marks 42. The indentation mechanism may be a conventional mechanism, for example having a resilient tongue whose head, bearing elastically on the side wall 32, penetrates into corresponding, regularly spaced recesses formed on the side wall 32.

The rotary ring 44 is preferably notched in order to facilitate its rotation by the operator.

Reading Instrument

The reading instrument can in particular be a compass, a magnetic compass as described in EP 2 192 944 or EP 2 218 952, or an electronic compass as described in EP 231 010.

Key

The key 16 has an actuator 50 and a booster 52 of axis Y (coincident with the axis X in the figures). One and preferably several helical springs 54 are interposed between the booster 52 and the actuator 50 so as to oppose their coming together along the axis Y.

The actuator 50 has a support 56 and a magnetic bar 58 of axis $\delta_{58}$ carrying a set of actuator magnets and secured to the support 56 by means of a flange 59 fixed to the support 56. The support 56 has the general shape of a discoidal plate 60 of axis Y.

A handle 62 protrudes from the upper surface $60_s$ of the plate 60, extending radially with respect to the axis Y. The handle 62 carries a magnetic orientation indicator 64 indicating the magnetic orientation of the magnetic bar 58. When the key is inserted into the locator receptacle 34 and is magnetically coupled to the micro-magnets 6 of the rotor 5, so as to drive it in rotation, the magnetic orientation indicator 64 points to the position mark 42 giving the opening pressure of the valve.

The lower surface $60i$ of the plate 60, being generally flat, defines a receptacle 66 receiving the magnetic bar 58, and reliefs 67 facilitating the fixing of the flange 59 to the support 56. The axis $\delta_{58}$ and the magnetic orientation indicator 64 are preferably coplanar with the axis Y. Observation of the magnetic orientation indicator 64 thus makes it possible to determine the orientation of the magnetic bar 58 about the axis Y.

The magnets 72 of the magnetic bar 58 are arranged in such a way as to produce a magnetic field capable of moving the rotor micro-magnets of the valve in order to unlock the rotor and then drive it in rotation. The arrangement of the magnets 72 must therefore be determined according to the position and arrangement of the micro-magnets 6 of the rotor of the valve.

Adapting the magnetic bar 58 according to the arrangement of the micro-magnets 6 for this purpose does not pose any particular difficulties.

Preferably, for optimum efficiency, the magnets 72 are arranged in such a way as to produce a magnetic field that is at a maximum in the plane passing through the axis Y and containing the axis $\delta_{58}$ of the magnetic bar or "maximum field plane".

Preferably, the magnets 72 are arranged in such a way that the magnetic field produced is symmetrical with respect to the maximum field plane and with respect to a plane perpendicular to the maximum field plane and passing through the axis Y.

Preferably, the set of magnets 72 has at least one, at least two, preferably three magnets whose North-South axis is radial with respect to the axis Y, called "radial magnets $72_r$".

Preferably, the set of magnets 72 has at least one, at least two, at least three, preferably four magnets whose North-South axis is parallel to the axis Y, or "longitudinal magnets" $72_1$.

Preferably, each radial magnet $72_r$ is sandwiched between two longitudinal magnets $72_1$. More preferably, along the axis $\delta_{58}$ of the magnetic bar, the magnets are in the following succession: $72_1$, $72_r$, $72_1$, $72_r$ (magnet centered on the axis Y), $72_1$, $72_r$ and $72_1$.

More preferably, when two magnets $72_1$ sandwich a radial magnet $72_r$, their magnetic orientation is reversed. In other words, the first of these longitudinal magnets has a North pole above the South pole, while the other of these magnets has a South pole above the North pole.

More preferably, when two radial magnets $72_r$ sandwich a longitudinal magnet $72_1$, their magnetic orientation is reversed. In other words, the poles of these radial magnets that face each other (separated by said longitudinal magnet) are of the same nature, for example are two North poles or two South poles.

Preferably, all the magnets 72 have a length, measured along the axis Y, that is identical.

Preferably, the width of a magnet 72, measured along the axis $\delta_{58}$, is smaller the closer the magnet 72 in question is to the axis Y. Preferably, the magnets 72 are arranged in a Halbach configuration. The inventor has found that this configuration is particularly effective.

Preferably, the actuator has a sole 74, preferably a substantially rectangular cube, on the lower face of which the magnets 72 are fixed. The sole 74 is preferably metallic and preferably extends in a plane perpendicular to the axis Y, preferably according to the axis $\delta_{58}$ of the magnetic bar.

Any displacement of the sole 74 in a plane perpendicular to the axis Y is impeded by the matching shape between the sole 74 and the receptacle 66 of the support 56 (see FIGS. 2b and 5b).

Any displacement of the sole 74 parallel to the axis Y is impeded by the sole 74 being clamped against the bottom of the receptacle 66, by means of fixing screws 82.

More specifically, the sole 74 extends laterally beyond the magnets 72 in such a way as to form two shoulders 83. The flange 59 is pierced by an orifice through which the magnets 72 can protrude from the lower surface of the flange 59. However, corner brackets are formed in the surface defining said orifice, in such a way that said corner brackets can bear on said shoulders 83. Each fixing screw 82 for fixing the flange 59 to the support 56 passes through an orifice 85 of the flange 59 and is screwed into a respective bore of the support. Each fixing screw 82 has a head 84 which abuts the substantially flat lower surface of the flange 59, in such a way as to press the sole 74 into the receptacle 66.

Figure 8:
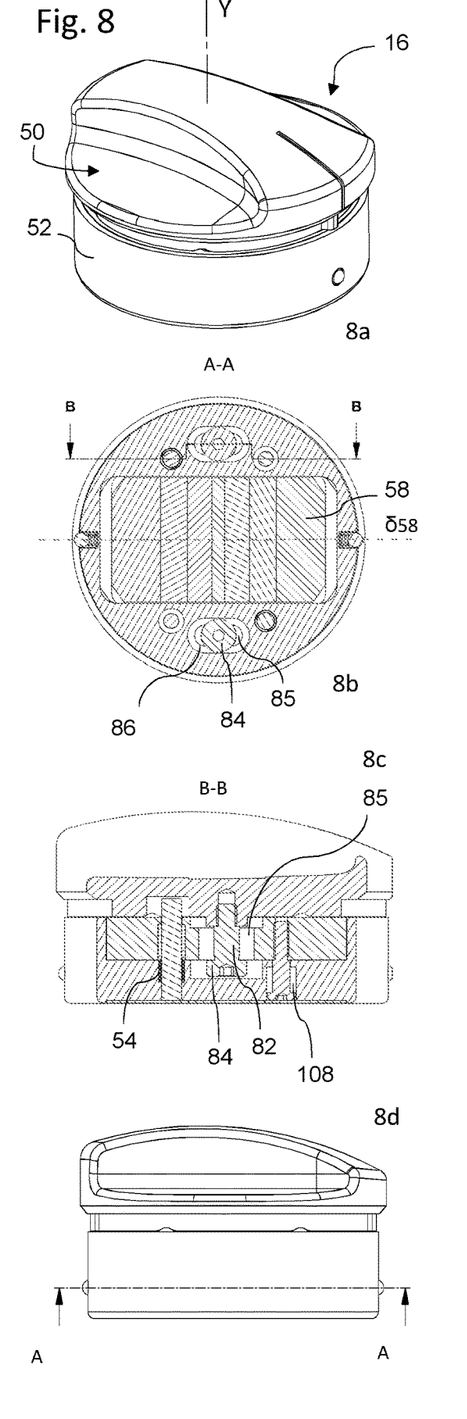
FIGS. 8 to 9 show the magnetic key of the device according to the invention from FIGS. 1 to 6, in lower and upper positions of the actuator, respectively.

In a preferred embodiment, the fixing of the flange 59 to the support 56 however permits a translation of the support, and therefore of the magnetic bar 58 rigidly fixed to the support 56, with respect to the flange 59, preferably along the axis $\delta_{58}$ of the magnetic bar. To this end, the orifice 85 is preferably of oblong cross section, the major axis of said cross section being parallel to the direction of translation (FIGS. 8b and 9b). As is shown in FIGS. 8b and 9b, the head 84 then bears only on the lateral edges 86 of the opening through which the orifice 85 opens out on the lower surface of the flange 59.

Booster

The booster 52 is intended to guide the translation of the actuator 50 along the axis Y.

It has a booster bottom 92 having the shape of a solid disk of axis Y, and a base 94 which, at the top, terminates in a skirt 96. The base 94 is pierced in such a way as to define, with the bottom 92, a cavity 98 that is suitable for receiving the set of magnets 72 when the actuator is driven along the axis Y.

The upper surface of the base 94 also defines orifices 97 for receiving the heads 84 of the screws for fixing the flange to the support.

The radially inner surface $96_{ri}$ of the skirt 96 and/or the side surface 981 of the cavity 98 guide(s) the driving of the actuator, along the axis Y, toward the bottom of the booster 92, by cooperation with the radially outer surface $59_{re}$ of the flange 59 and the side surface $72_1$ of the set of magnets 72, respectively.

Preferably, the actuator is movable only in translation along the axis Y with respect to the booster, preferably by cooperation of the side surfaces $98_1$ and $72_1$.

The number of springs 54 is not limited. Preferably, it is greater than 2, greater than 3 or greater than 4, and/or less than 10. The springs are preferably distributed at uniform angles about the axis Y. More preferably, they extend substantially parallel to the axis Y, which optimizes their effectiveness.

More preferably, each spring 54 is engaged on a guide rod 99 which is fixed to the booster or to the actuator and which, when the actuator is driven into the booster, slides in a corresponding receptacle provided on the actuator or the booster, respectively, as is shown in FIGS. 8c and 9c.

Figure 9:
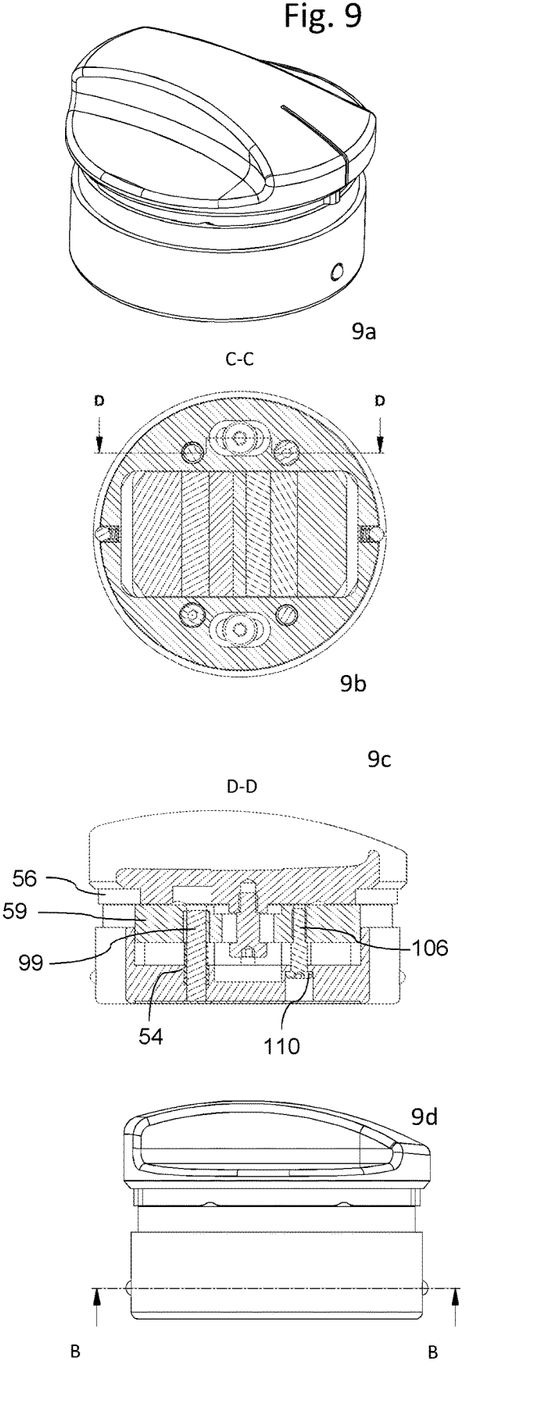

Preferably, the booster is maintained rigidly connected to the actuator, for example by fixing screws 106 on the flange 59 through an orifice 108 provided in the booster, as is shown in FIGS. 8c and 9c. The orifice 108 is preferably configured to guide the sliding of the head 110 of the screw 106 parallel to the axis Y, while serving as a second stop for defining the upper position of the actuator, as is shown in FIG. 9.

The springs 54, which are helical springs, are interposed between the actuator 50 and the booster 52, in such a way as to oppose the driving of the actuator into the booster. At rest, that is to say in the absence of an insertion push applied to the actuator, the springs 54 hold the actuator at the second insertion depth (upper position of the actuator shown in FIG. 9).

Operation

The operation of the device results directly from the above description.

Figure 1:
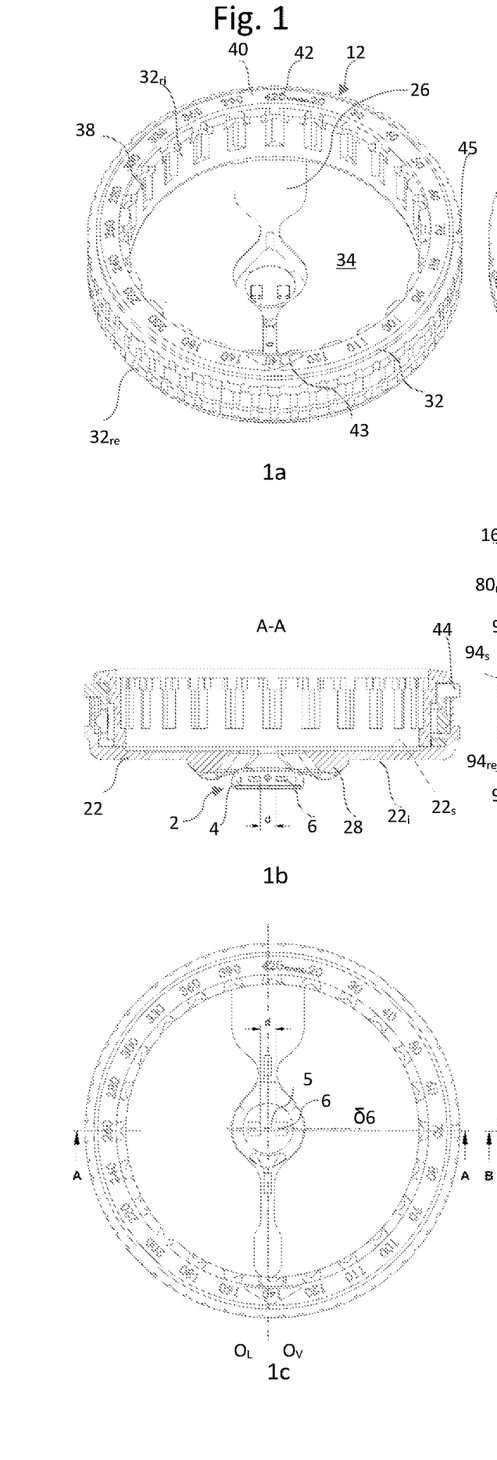
FIGS. 1 to 6 show a device according to the invention in configurations successively adopted in the implementation of a method according to the invention.

In the initial position shown in FIG. 1, the two micro-magnets of the rotor of the valve are spaced apart from each other by a distance d, in an "approximated" position. Preferably, this approximated position results from the mutual attraction of the two micro-magnets.

In the approximated position, the two micro-magnets preferably maintain respective locking lugs of the rotor in cavities of the chamber, thus preventing any rotation of the rotor. This embodiment can, for example, correspond to FIGS. 1 and 2 of EP 688 575. The approximated position of the micro-magnets is therefore a locking position of the rotor of the valve.

The skin of the patient has not been shown in the various figures.

The valve can in particular be placed under the skin of the cranium, the neck, the clavicular fossa, the back or the hips.

The actuator magnet is preferably configured to exert a magnetic field designed, when the valve is in the open air and the locator is placed perpendicular to the rotation axis of the rotor of the valve, at a distance from the valve of greater than 2 mm, greater than 3 mm, greater than 5 mm, greater than 8 mm and/or less than 30 mm, less than 25 mm, less than 20 mm, less than 15 mm, less than 12 mm or less than 10 mm, to unlock the rotor at the first insertion depth and to be rotationally coupled to the rotor at the second insertion depth.

The valve 2 being implanted, it extends between the valve 2 and the bottom of the locator 12. The valve is therefore not visible to the operator, although the latter can locate it by palpation.

At step a), the operator has to precisely locate the valve 2 and position the locator accordingly.

To this end, he places the locator 12 against the patient's skin, in such a way as to place the valve in the window 26 of the locator. The valve 2 then penetrates slightly, by deformation of the skin, into the window 26 of the locator.

The orientation axis $O_V$ of the valve then extends parallel to the orientation axis $O_L$ of the locator. In addition, the rotation axis R of the rotor is then substantially coincident with the axis X of the locator receptacle.

The rotation axis R of the rotor can pass through the center of the valve body. Alternatively, it can be slightly offset from the center of the valve body, and thus from the longitudinal axis $O_V$ of the valve, in particular in order to form, between the rotor and the valve body, a space for accommodating the elastic return member bearing on the shutter. As a result, the axis X of the locator receptacle may not intersect the orientation axis $O_L$ of the locator (longitudinal axis of the window 26).

The alignment marker 43 allows the locator to be oriented in the direction of flow of the liquid.

An orientation of the locator with respect to the valve is described for example in EP2 192 944.

To modify the angular position of the rotor, the operator proceeds as follows:

At step b), the operator determines the angular position of the rotor of the valve about its axis using the reading instrument, for example a magnetic compass.

In a known manner, as described in EP 2 192 944, the compass is preferably introduced into the locator receptacle, in such a way that the rotation axis of the compass needle is centered on the axis X of the locator receptacle, which itself is substantially centered on the rotation axis R of the rotor of the valve. Preferably, the compass is also used to improve the precision of the positioning of the locator, so that the rotation axis R of the rotor is coincident with the axis X of the locator receptacle.

The compass needle is then oriented along the axis $\delta_6$ of the two micro-magnets 6, which is radial with respect to the rotation axis R of the rotor. In FIG. 1a, it appears that the position marker 45 is then aligned with the position mark "70".

Preferably, the operator locates the axis $\delta_6$ by turning the rotary ring 44 in such a way as to align the position marker 45 with this axis. The operator can thus memorize that the opening pressure of the valve, in the initial configuration, is in this case 70 mmH$_2$O.

He then withdraws the compass from the locator receptacle.

The following steps are intended to modify the opening pressure in such a way that it reaches a desired opening pressure of 140 mmH$_2$O, for example.

At step c), the operator places the actuator such that the magnetic orientation indicator 64 is directed to the position marker 45 "70" indicating the orientation of the axis $\delta_6$ of the micro-magnets of the valve. The axis $\delta_{58}$ of the magnetic bar is then coplanar with the axis $\delta_6$ of the micro-magnets and coplanar with the axis Y.

The key 16 is then inserted into the locator receptacle along the axis X. This insertion is guided by the contact between the radially outer surface 94$_{re}$ of the base of the booster and the radially inner surface 32$_{ri}$ of the side wall 32 of the locator. The insertion continues until the booster comes into abutment with the bottom 22 of the locator. As is shown in FIG. 2b, the bottom 92 of the booster rests, preferably over substantially its entire surface, on the bottom 22 of the locator.

Figure 2:
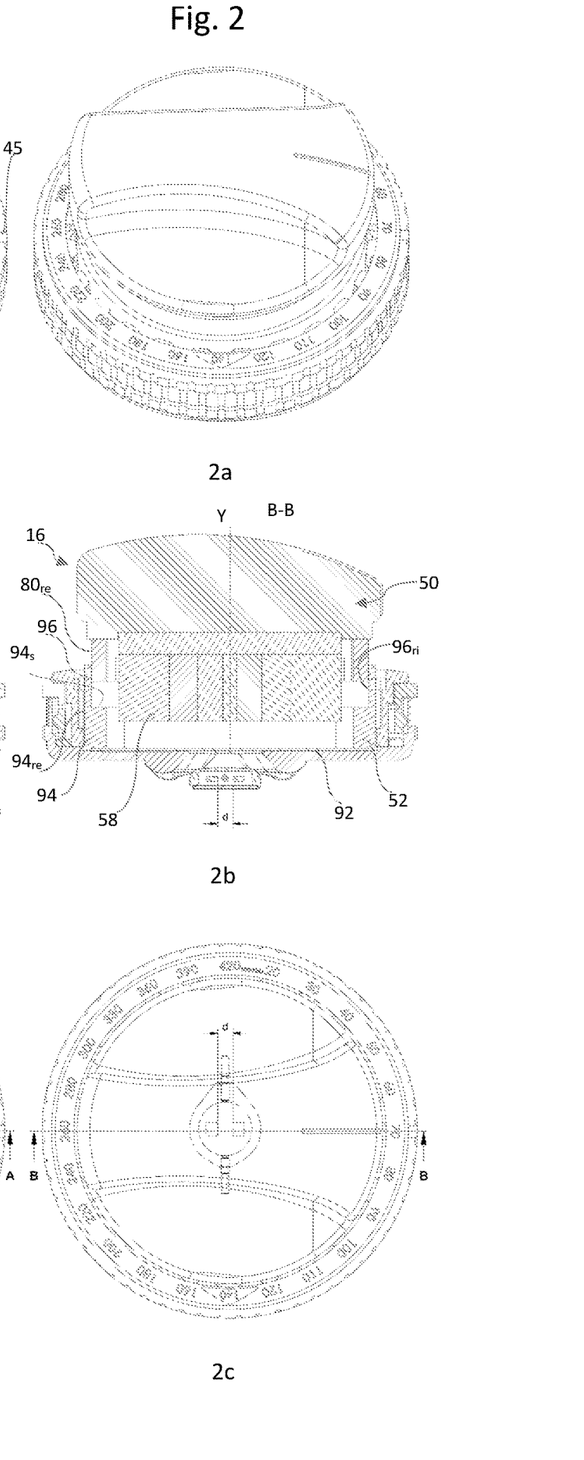

The springs 54 then oppose the insertion of the actuator into the booster (FIG. 2).

In this position of the actuator, called the "upper position", the magnets 72 are too distant to space apart the micro-magnets of the rotor from one another.

Figure 3:
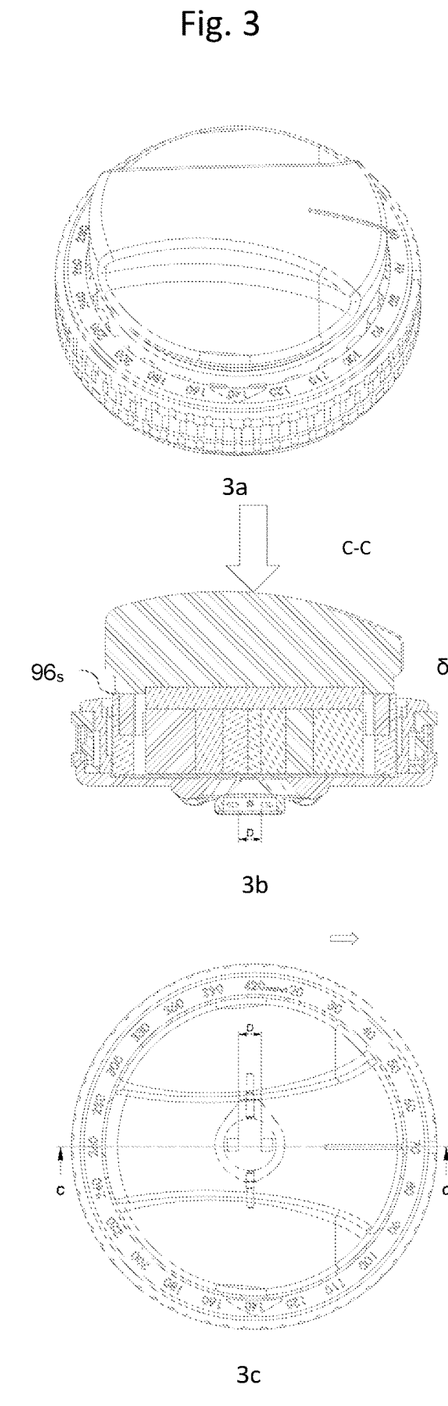
Figure 4:
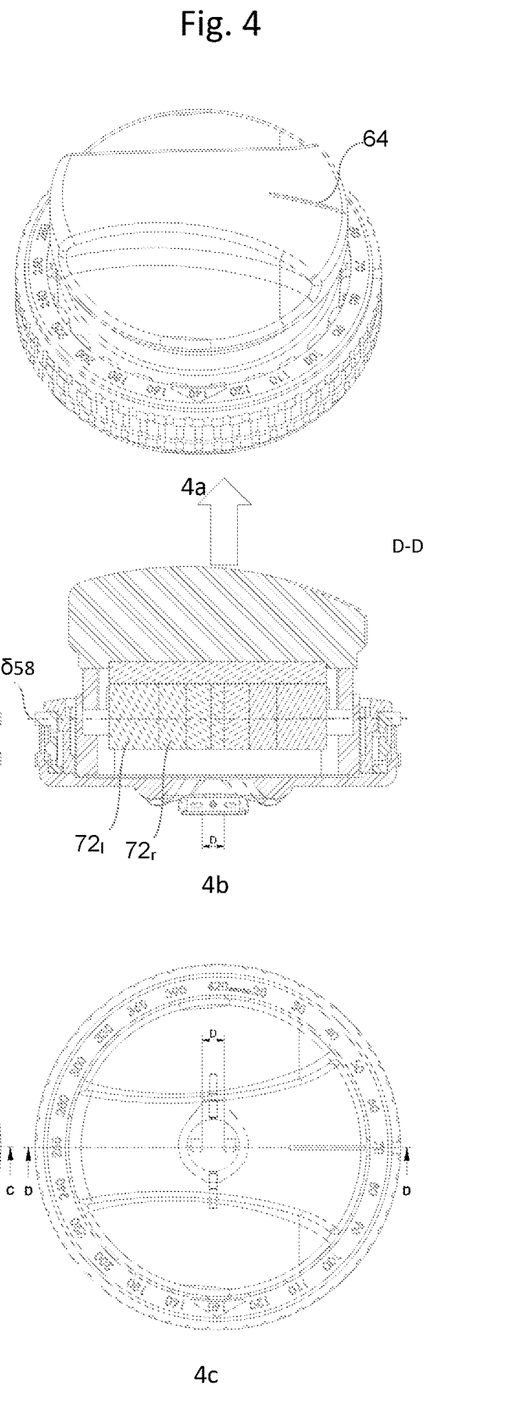

The operator then exerts an insertion push, along the axis Y, in order to continue the insertion of the actuator into the actuator hole, by sliding it on the booster, as far as the first insertion depth (arrow in FIG. 3). The actuator is then in the "lower position".

The first insertion depth advantageously corresponds to a maximum insertion, determined by the actuator coming into abutment with the booster, for example by the actuator coming into contact with the edge 96$_s$ of the skirt 96, and/or the upper surface 94$_s$ of the base 94 of the booster and/or the bottom 92 of the booster and/or the bottom of orifices for receiving the heads of fixing screws of the flange, as is shown in FIG. 3b. The edge of the skirt 96, the upper surface of the base 94, the bottom of the booster and the bottom of the receiving orifices are examples of a "first stop" determining the first insertion depth of the actuator.

Alternatively, the booster could be without a bottom, and the magnets 72 could come into abutment with the bottom of the locator, which would then constitute a first stop determining the first insertion depth.

At the first insertion depth, and after aligning the magnetic orientation indicator 64 with the position marker 45, the magnets 72 of the actuator are close to the micro-magnets of the rotor and exert a sufficiently strong magnetic field to space these apart from one another. The distance between the two micro-magnets increases to a value D. The action of the micro-magnets then no longer impedes the rotation of the rotor. The micro-magnets thus pass from the approximated position (FIGS. 1 and 2), in which the rotor is locked, to a spaced-apart position (FIGS. 3 to 5), in which the rotor is unlocked.

Preferably, before turning the actuator, the operator moves the handle along the axis $\delta_{58}$ of the magnetic bar. This movement causes that of the magnets 72 of the actuator, which acts on the micro-magnets of the rotor that are coupled to them. By repeating these movements in one direction and then the other (movement to and fro), the operator can thus slightly shake and, if necessary, alternately unblock the micro-magnets, which facilitates their unlocking.

The rotation of the actuator, inserted to the first insertion depth in the locator receptacle, allows the rotor of the valve to be driven in rotation. However, this driving is not always reliable.

At step d), according to the invention, the operator partially removes the actuator from the locator receptacle, as far as the second insertion depth, defined by the rest position of the springs 54.

To partially remove the actuator from the locator receptacle, it thus suffices for the operator to release the pressure on the actuator. The latter then rises, under the effect of the springs 54, as far as the rest position shown in FIG. 4, identical to the position in FIG. 2.

As is shown in FIG. 4b, the micro-magnets of the valve remain however in the spaced-apart position. Without being bound by this theory, the inventor explains this phenomenon by the necessity to exert a greater force for spacing the micro-magnets apart from each other (unlocking) than for keeping them in the spaced-apart position.

Surprisingly, the inventor has also found that, in the position of the actuator corresponding to the second insertion depth, shown in FIG. 4b, the driving in rotation of the unlocked rotor was much more reliable than in the position of the actuator corresponding to the first insertion depth, shown in FIG. 3.

In the example shown, the second insertion depth of the actuator is therefore determined by the booster, which thus constitutes a "second insertion stop".

The assembly composed of the booster and the springs at rest also forms a guide for the rotation of the actuator 50 about the axis X, in a plane perpendicular to the axis X. Whatever the angular position of the actuator, the springs in fact oppose continued insertion of the actuator.

Figure 5:
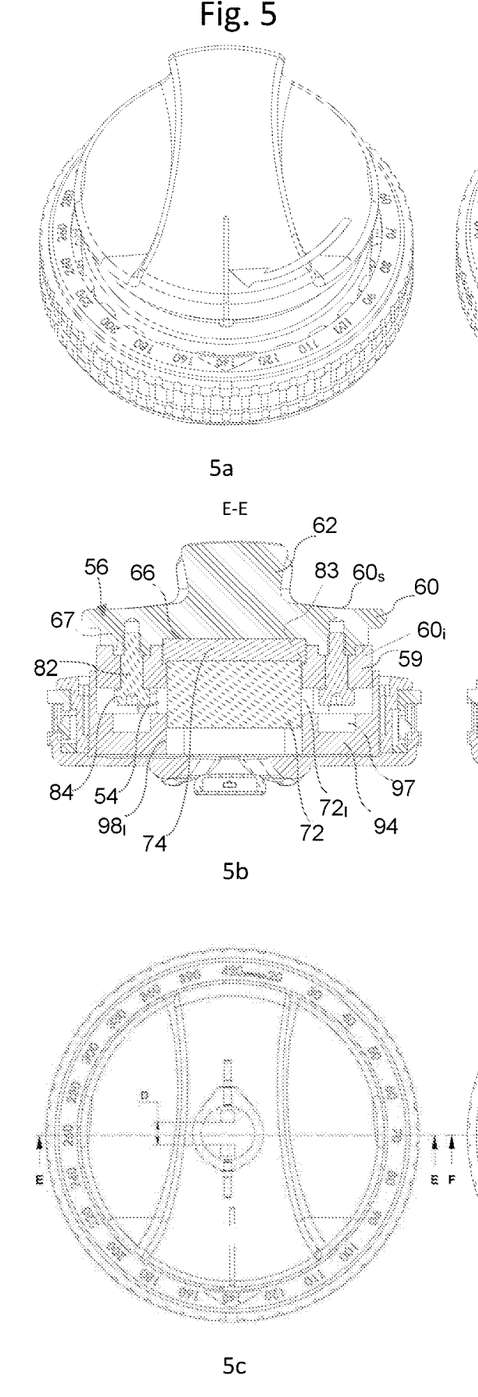

At step e), the operator can turn the key to a position corresponding to the desired opening pressure, shown in FIG. 5 and corresponding, for example, to 140 mmH$_2$O. The springs 54 advantageously allow the operator to maintain the insertion depth of the actuator at the second insertion depth. Reliability is thereby improved.

A set of magnets 72 arranged in a Halbach configuration advantageously permits particularly reliable unlocking of the rotor and particularly reliable driving in rotation of the rotor.

Figure 6:
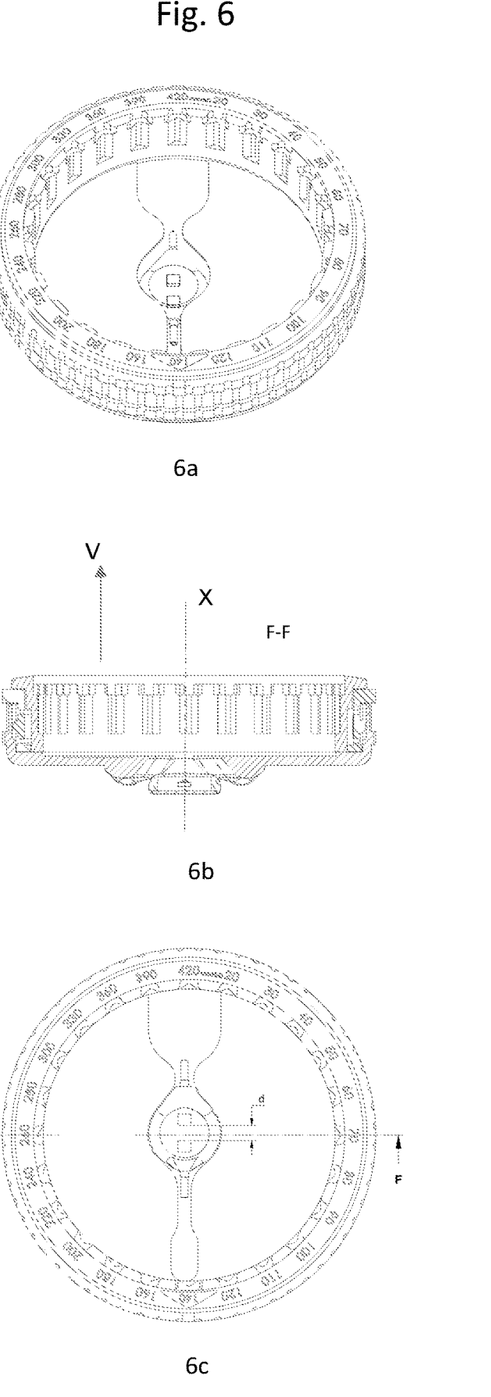

At step f), the operator distances the actuator from the valve. The forces of approximation of the micro-magnets then once again become greater than the spacing forces generated by the actuator, which leads to them coming closer together, as far as the distance d, in which they lock the rotor in rotation, as is shown in FIG. 6.

In one embodiment, the rotation of the magnetic key is indexed with respect to the locator, in such a way that the magnetic orientation indicator 64 can only be positioned opposite a position mark 42. Preferably, the indentation is determined such that, when the action of the actuator on the micro-magnets becomes low and the micro-magnets tend to come closer together, the lugs are substantially opposite a cavity of the valve body and are able to penetrate into these cavities under the effect of the mutual closing-together of the micro-magnets.

To space the actuator apart from the valve, the actuator can be withdrawn from the locator.

As is clear now, the invention affords a simple and reliable solution for adjusting the opening pressure of a valve whose rotor is lockable by means of micro-magnets. However, the invention is of course not limited to the embodiments described and shown, which are provided for illustrative purposes only.

In particular, means other than the booster could be used to determine the first and second insertion depths.

The booster is not necessarily rigidly connected to the actuator.

The booster could be integrated in the locator.

In one embodiment, the rotation of the actuator does not bring about that of the booster.

Figure 7:
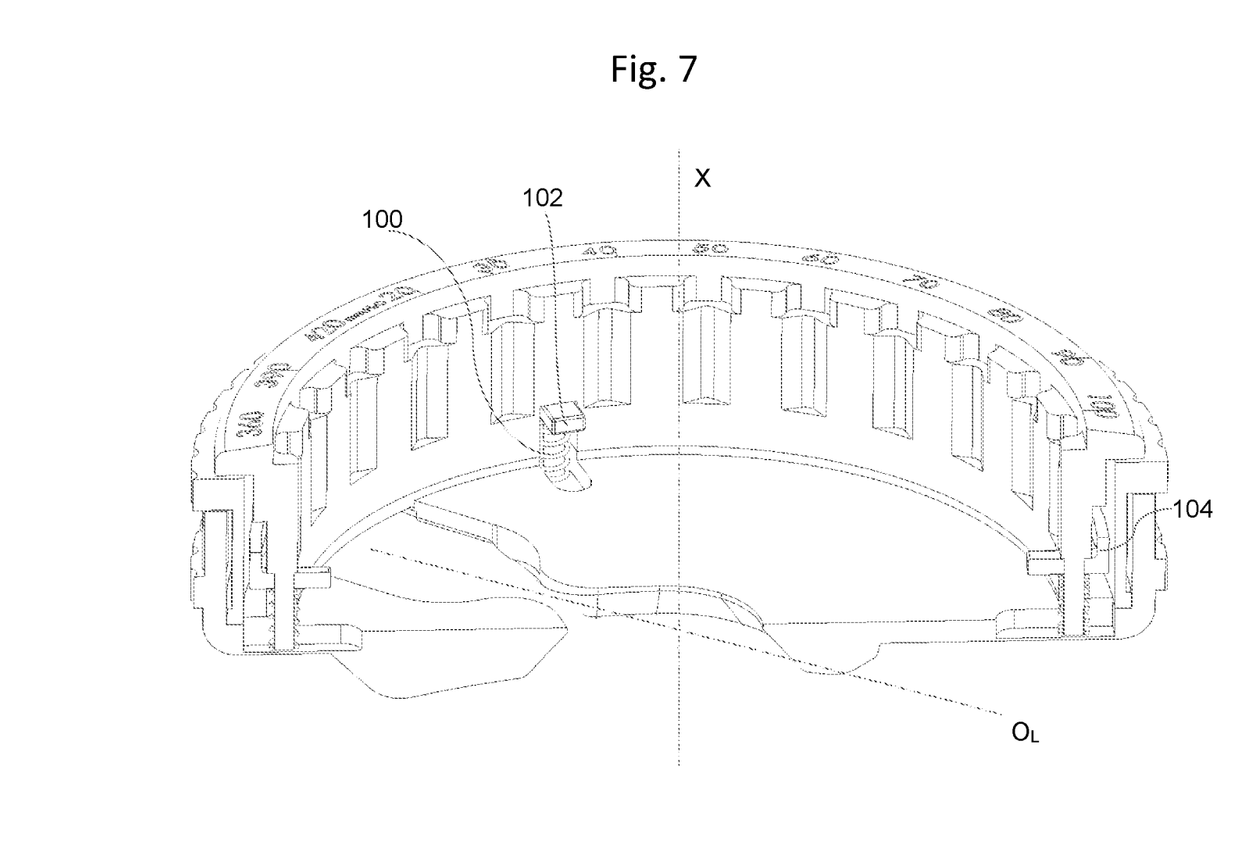
FIG. 7 shows a perspective view of a locator in a second embodiment of the invention.

As is shown in FIG. 7, springs 100 equivalent to the springs 54 could bear directly on the locator, for example on the bottom of the locator, with the booster then becoming optional.

In the embodiment shown in FIG. 7, springs are for example accommodated within the thickness of the side wall of the locator. Each spring carries a tab 102, which bears on the end of the spring opposite the end bearing on the locator, and which protrudes inside the locator receptacle. Under the effect of the springs, the tabs thus oppose the insertion of the actuator beyond the second insertion depth.

Preferably, the tabs can retreat into the bottom of the locator, which allows the magnets to be as close as possible to the valve at the first insertion depth.

In the embodiment shown, the tabs are connected to each other by a circular ring 104, which is movable in an annular space, of axis X, formed in the side wall of the locator.

In one embodiment, the first insertion depth and/or the second insertion depth are defined by stubs, for example in the form of balls, protruding elastically from the side wall of the locator or the actuator under the effect of springs preferably extending radially with respect to the axis X. Upon entering corresponding recesses of the actuator or of the locator, respectively, the stubs can thus oppose a movement of the actuator, along the axis X, from the first insertion depth and/or the second insertion depth. However, the stubs can preferably retreat into the side wall of the locator or of the actuator under the effect of an insertion push and/or a withdrawal pull exerted by the operator on the actuator.

The features of the various embodiments, particularly of the embodiments shown, can be combined, unless there is technical incompatibility.

REFERENCES USED IN THE FIGURES

2: valve
4: valve body
5: valve rotor
6: micro-magnets of the rotor
12: locator
16: magnetic key
22: bottom of the locator
26: window in the bottom of the locator
28: reliefs
32: side wall of the locator
34: locator receptacle
38: guide groove
40: reading zone
42: position marks carried by the reading zone 40
43: alignment marker
44: rotary ring of the locator
45: position marker carried by the rotary ring 44
50: actuator
52: booster
54: springs interposed between booster and actuator
56: support
58: magnetic bar of the actuator
59: flange fixing the magnetic bar 58 to the support 56
60: actuator plate
62: actuator handle
64: magnetic orientation indicator
66: receptacle of the plate 60 receiving magnetic bar 58
67: relief for fixing the flange to the support
72: actuator magnets
74: sole
83: shoulder
82: screw for fixing the flange to the support
84: heads of screws for fixing the flange to the support
85: orifice for fixing the flange to the support
86: lateral edge of the opening via which the orifice 85 opens on the lower surface of flange 59
92: bottom of booster
94: base of the booster
96: skirt of the booster
97: orifices for receiving the heads of the screws
98: cavity formed in the base 94
99: guide rod of spring
100: springs of the locator
102: tabs pushed by the springs of the locator
104: circular ring connecting the tabs
106: screw for fixing the booster to the flange
108: orifice for fixing the booster to the flange
110: head of screw 106
X: axis of the locator receptacle
Y: axis of the magnetic key
R: rotation axis of the rotor of the valve
$O_V$: longitudinal axis of the valve
$O_L$: longitudinal axis of the window of the locator
$\delta_6$: axis of the micro-magnets of the rotor
$\delta_{58}$: axis of the magnetic bar

The invention claimed is:

1. A treatment device having
an implantable valve having:
  a body defining an internal chamber,
  an admission conduit and a discharge conduit that are formed in the side wall of said internal chamber and are able to be connected, respectively, to a liquid delivery catheter and a liquid drainage catheter,
  a rotor able to turn in said internal chamber about a rotation axis, the rotor having at least one micromagnet movable between positions of locking and unlocking of the rotor, in which positions it respectively prohibits and permits the rotation of said rotor, a rotation of the rotor modifying the opening pressure of the valve,
  a shutter,
  an elastic return member compressing the shutter in its seat in such a way as to regulate and, if appropriate, block the passage of liquid into the internal chamber,
a device for adjusting the opening pressure of said valve, the adjustment device having:
  a valve locator defining a locator receptacle of axis X;
  a key having an actuator with an actuator magnet, the actuator being insertable, along the axis X, into the locator receptacle to a first insertion depth and to a second insertion depth less than the first insertion depth, the adjustment device having a guide for guiding the rotation of the actuator about the axis X from at least one angular position of the actuator about the axis X in which the actuator is at the second insertion depth,
the actuator magnet exerting a magnetic field designed, when the locator is placed against the skin of a patient under which the valve has been implanted, the valve being placed in a window of the locator, to unlock the rotor at the first insertion depth and to be rotationally coupled to the rotor at the second insertion depth.

2. The treatment device as claimed in claim 1, in which the guide is configured to guide the rotation of the actuator about the axis X from any angular position of the actuator about the axis X in which the actuator is at the second insertion depth, in a rotation plane substantially perpendicular to the axis X.

3. The treatment device as claimed in claim 1, in which the difference between the first and second insertion depths, measured along the axis X, is greater than 5 millimeters.

4. The treatment device as claimed in claim 1, having first and second stops defining the first and second insertion depths, respectively.

5. The treatment device as claimed in claim 1, in which the key has a booster on which the actuator is mounted movably in translation along an axis Y of the key, which axis Y coincides with the axis X of the locator receptacle when the key is inserted into the locator receptacle.

6. The treatment device as claimed in claim 5, having a spring interposed between the actuator and the booster or a spring interposed between the actuator and the locator, so as to oppose an insertion of the actuator, along the axis Y, beyond the second insertion depth.

7. The treatment device as claimed in claim 6, in which said one spring extends along an axis parallel to the axis X and/or the axis Y or in a plane perpendicular to the axis X or the axis Y.

8. The treatment device as claimed in claim 6, in which said spring is accommodated in a receptacle and, at the side of the receptacle opening, is configured in such a way as to push a stub toward the axis X or toward the axis Y.

9. The treatment device as claimed in claim 5, in which the actuator is guided in translation on the booster along the axis Y.

10. The treatment device as claimed in claim 1, in which the actuator has a set of magnets arranged in a Halbach configuration.

11. The treatment device as claimed in claim 5, in which the actuator has a support on which said actuator magnet is rigidly fixed, a flange mounted movably in translation, along the axis Y, with respect to the booster, and means to prevent any displacement of the support, along the axis Y, with respect to the flange, while permitting a displacement of the support perpendicularly to the axis Y, with respect to the flange.

12. The treatment device as claimed in claim 1, in which the actuator magnet is configured to exert a magnetic field designed, when the valve is in the open air and the locator is placed perpendicularly to the rotation axis of the rotor of the valve, to unlock the rotor only when the actuator magnet is at a distance from the rotor of less than 20 mm; and/or to be rotationally coupled to the rotor only when the actuator magnet is at a distance from the rotor of less than 30 mm.

* * * * *